United States Patent [19]

Ackerman et al.

[11] Patent Number: 5,346,903
[45] Date of Patent: Sep. 13, 1994

[54] AQUEOUS SUSPENSION PREPARATION FOR INJECTION, METHOD FOR PRODUCING THE SAME AND USE THEREOF FOR PRODUCING PAIN RELIEF

[75] Inventors: Eric W. Ackerman, Am Nuenen; Rene J. E. Grouls; Hendrikus H. M. Korsten, both of Eindhoven, all of Netherlands

[73] Assignee: Stichting Catharina Ziekenhuis, Netherlands

[21] Appl. No.: 979,128

[22] Filed: Nov. 20, 1992

[30] Foreign Application Priority Data

Mar. 20, 1990 [NL] Netherlands ............. 9000634

[51] Int. Cl.$^5$ ............................ A61K 31/485
[52] U.S. Cl. ................... 514/282; 514/567; 514/975; 424/400
[58] Field of Search ........... 514/282, 567, 975; 424/400

[56] References Cited

U.S. PATENT DOCUMENTS

| | | | |
|---|---|---|---|
| 4,599,354 | 7/1986 | Shulman | 514/530 |
| 4,963,367 | 10/1990 | Ecanow | 424/485 |

FOREIGN PATENT DOCUMENTS 0031603  7/1981  European Pat. Off. ... A61K 31/245
784659  10/1957  United Kingdom .

OTHER PUBLICATIONS

Gafitanu et al., *Chemical Abstracts*, CA100(10:73840s, 1982.
Korsten et al., *Anesthesiology*, 75: 950–960 (1991).

*Primary Examiner*—Marianne M. Cintins
*Assistant Examiner*—William R. A. Jarvis

[57] ABSTRACT

The present invention relates to an aqueous suspension preparation for injection and to a method for producing the same and further relates to the use of said preparation for producing pain relief. The invention particularly relates to a preparation as indicated hereinabove, comprising a water-insoluble local anesthetic and/or narcotic analgesic suspended in an aqeuous medium, which preparation can be succesfully used for epidural and intrathecal pain relief and for conduction anesthesia and infiltration anesthesia. The preparation is stabilized by the addition of a non-ionic surface-active agent in an amount of less than 1 wt. %. The particles of the water-insoluble active agent have a mean particle diameter of less than 20 $\mu$m. More than 99% of the particles have a diameter of less than 100 $\mu$m and more than 90% have a diameter of less than 50 $\mu$m.

16 Claims, No Drawings

AQUEOUS SUSPENSION PREPARATION FOR INJECTION, METHOD FOR PRODUCING THE SAME AND USE THEREOF FOR PRODUCING PAIN RELIEF

This application is a continuation of International Application No. PCT/NL91/00042, filed on Mar. 20, 1991, designating the United States of America.

The present invention relates to an aqueous suspension preparation for injection and to a method for producing the same and further relates to the use of said preparation for producing pain relief. The invention particularly relates to a preparation as indicated hereinabove comprising a waterinsoluble local anesthetic and/or narcotic analgesic suspended in an aqueous medium, which preparation can be succesfully used for epidural and inthrathecal pain relief and/or for conduction anesthesia and infiltration anesthesia.

With "water-insoluble" is meant in the present case that less than 0.01 g of said substance is soluble in 1 ml of water, usually less than 0,001 g. According to the Dutch Pharmacopeia (Ed. VIII) such substances are designated as being difficultly soluble (0,001–0.01 g/ml), very difficultly soluble (0.0001–0,001 g/ml) or almost insoluble (less than 0.0001 g/ml ).

U.S. Pat. No. 4,599,354 discloses a preparation for epidural pain relief which preparation has been based on an aqueous medium in which a water-insoluble local anesthetic, in particular the n-butyl ester of p-aminobenzoic acid (hereinafter designated with the abbreviation BAB) has been suspended. The water comprises polyethylene glycol (PEG) as suspending agent in an amount up to 10 wt. %. In the example given 2.3 wt. % PEG is used. The preparation further comprises NaCl to make the aqueous medium isotonic and moreover a little hydrochloric acid is added to provide a pH of 4. In this patent nothing is said about the particle size of BAB.

In practice the stability of the known suspension preparation appears to leave much to be desired. The preparation is to be used within a relatively short time as otherwise sedimentation and agglomeration of the particles of the active agent is going to start which in use can lead to clogging of injection needles or injection catheters. In producing this preparation another problem arises in connection with sterilisation. Sterilisation is usually carried out at about 120° C., a temperature lying far above the melting point of BAB (57° C.). thus, this substance will melt and on solidification after cooling vigorous stirring should be performed to regain the suspension. In practice the stability appears to be poorer than prior to sterilisation due to a change in the range of particle diameter and/or the mean particle diameter, probably caused by the fact that relatively more larger particles are present.

British patent 784659 also discloses aqueous suspensions of medicinal agents in which polyalkylene glycols, for example PEG, are used as suspending agents. These suspensions can be administered parenterally. According to page 3, lines 28–51, of this patent it is recommended in some instances to provide in addition to said suspending agent a non-ionic surface active agent, for example polyoxy-alkylene ethers of partial higher fatty acid esters of polyhydroxy alcohols, e.g. the sorbitan derivatives Tween 20 or Tween 80, while further various other additions are proposed such as a lubricant, a preservative, an isotonic agent and/or a buffer (page 3, lines 76 and following). The greater the number of added auxiliaries is, the greater is the risk that side-effects occur on use in human beings. This British patent also discloses that in the aqueous suspensions of medicinal agents in which a polyalkylene glycol, i.g. PEG, is used as suspension agent, the particles should be less than 80 μm in size and for ophthalmic use substantially of all the particles should be less than 20 μm and preferably less than 10 μm in size.

It is further to be noted that U.S. Pat. No. 3,337,400 discloses an aqueous suspension of a water-insoluble glucocorticoid in which a water-soluble, injectable local anesthetic and an antibiotic are present. As suspending agent to be used PEG is considered first (see the examples), while moreover preferably an isotonic agent (sodium chloride, dextrose and the like) and a preservative are present. Thus, this patent deals with an injectable, aqueous suspension in which three drugs have been combined in which the corticoid is present in suspended form and possibly also the antibiotic. No reference is made to water-insoluble anesthetics.

It is also to be noted that Dutch patent application 6709708 discloses pharmaceutical preparations for the treatment of arteriosclerotic, atherosclerotic and similar metabolic anomalies in mammals. The disclosed injectable aqueous solutions for that purpose comprise an organic local anesthetic and a hydrolysis inhibitor for said anesthetic. Examples of the hydrolysis inhibitor are polyvinyl pyrrolidone, methylcellulose, dextran, gelatin or polyoxyethylene sorbitanmono-oleate. Preferably polyvinyl pyrrolidone is used. The amount by weight of hydrolysis inhibitor is at least 3 times the amount by weight of the local anesthetic in the solution.

In this Dutch patent application, also some water-insoluble local anesthetics, e.g. BAB, are disclosed for use in the preparations for the treatment of arteriosclerotic, atherosclerotic and similar metabolic anomalies, but nowhere in the description of said patent application any reference is made to suspensions and the way suspensions could be prepared for the indicated use. In that respect Dutch patent application 6709708 does not add anything to the state of the art.

When local anesthetics and/or narcotic analgesics are to be used for epidural or intrathecal pain relief, injection or administration of water-soluble anesthetics and/or narcotic analgesics through a catheter is the most simple way. The substances can be administered in an aqueous medium, for example in an isotonic solution. However, an objection of such solutions is that they rapidly loose their activity and the administration must be repeated several times or must be carried out continuously. Similar objection exists as to water-insoluble anesthetics when administered in a solvent, for example in glycerol or in an oil in which these substances are soluble. Also in that case the substances loose their activity relatively soon, while moreover there is a great risk that the active agent spreads in the body to a greater extent than desirable and/or the solvent gives serious side-effects.

A suitable injectable suspension of the active agent has the advantage that the effect thereof is much prolonged, because the active agent is dissipated from the injection site to the surrounding tissue very slowly and therefore can be active for a long period. However, production and use of a suspension of the active agent give the problems mentioned above with respect to the stability and the possible side-effects of the auxiliaries. For example, PEG appears to be neurotoxic. According to the present invention said problems can be solved or markedly be reduced.

The inventors surprisingly found that very stable suspensions of water-insoluble local anesthetics and/or narcotic analgesics can be prepared by suspending these substances having suitable particle sizes in an aqueous medium, for example water or an isotonic salt solution, in the presence of a relatively minor amount of one or more nonionic surface-active agents, as sole agent for stabilizing the suspension in particular sorbitan derivatives such as the polyoxyethylene sorbitan derivatives of fatty acids, also known under the generic designation polysorbate followed by a number indicating the specific composition.

The invention thus relates to the new suspensions so obtained.

As water-insoluble anesthetics those of the ester type have to be considered in the first place, for example the alkyl esters of p-aminobenzoic acid, such as BAB, PAB (n-propyl ester of p-aminobenzoic acid) and EAB (ethyl ester of p-aminobenzoic acid, benzocaine). BAB is preferred in connection with the use for epidural pain relief. Also other water-insoluble local anesthetics of the estertype and of the amidetype as well as water-insoluble salts thereof can be used for producing stable aqueous suspensions according to the invention, such as lidocaine base, tetracaine base, bupivacaine base and water insoluble salts of these bases, such as picrates and iodides.

As water-insoluble narcotic analgesics the natural and (semi-)synthetic opioids as well as water-insoluble salts thereof can be used for producing stable aqueous suspensions according to the invention, such as morphine, buprenorphine and fentanyl.

The local anesthetics which can be used for producing the stable aqueous suspensions according to the invention are also designated as local analgetics because of their use for pain relief.

The water-insoluble local anesthetics and/or narcotic analgesics should have a suitable particle diameter, that is to say, the particles should predominantly (i.e. for more than 99%) have a diameter of less than 100 $\mu$m. More than 90% of the particles should have a diameter of less than 50$\mu$, and the mean particle diameter should be below 20 $\mu$m.

The amount of water-insoluble local anesthetic and/or narcotic analgesics in the suspension may vary from 1 to 15 wt. % and is preferably about 10 wt. %, that is to say, about 0.1 g/ml.

Surprisingly only a small amount of said non-ionic surface-active agents is necessary to obtain a stable aqueous suspension of said water-insoluble local anesthetic and/or narcotic analgesics having said particle size, i.e. less than 1 wt. %. In almost all cases the percentage can be substantially less and an amount of less than 0.4 wt. % will suffice and is preferably in the range of 0.01 to 0.2 wt. %. The amount may vary, of course, with the amount of active agent to be suspended.

As an illustration: a stable suspension can be produced from 1 g BAB or morphine in powder form having a mean particle size of about 15 $\mu$m using 10 ml of a physiological salt solution (0.9 wt. % NaCl) containing 2.5 mg polysorbaat 80 (about 0,025 wt. %).

Preferred non-ionic surface active agents are polyoxyethylene ethers of polyhydroxyalcohols partially esterified with higher fatty acids. Examples thereof are the sorbitan derivatives polysorbate 20, polysorbate 40, polysorbate 60, polysorbate 80, polysorbate 85. Especially polysorbate 80 gives excellent results.

Also polyhydroxyalcohols (partially) esterified with higher fatty acids such as sorbitol derivatives can be used.

The pH of the suspension of a local anesthetic obtained according to the invention is usually in the range of 3 to 7 and mostly no adjustment is required prior to the use of the suspension for pain relief. In the above illustrative example of a BAB-suspension with polysorbate 80 in a physiologocal salt solution the pH value is 6.5 and no adjustment is required. Using a diluted glucose solution instead of a physiological salt solution as aqueous medium, the pH thereof is adjusted to about 5.5, if necessary.

The pH of the suspension of a narcotic analgesic is adjusted to the pH value at which optimal stability of the suspension is obtained. This value differs for each narcotic analgesic. For the suspension of morphine pH is adjusted to a value in the range 9–11.

For suspensions in which a local anesthetic and an opioid analgesic are combined the optimal pH value varries according to the substances used. By varying the pH in these suspensions the absolute and relative minor concentrations of dissoluted local anesthetic and narcotic analgesic can be manipulated.

The suspensions according to the invention can be produced in various ways. When the starting material, i.e. the local anesthetic and/or narcotic analgesic in powder form, does not have the required particle size, the powder is subjected to a milling operation until it has the particle size distibution as indicated hereinbefore. Subsequently the active agent in powder form is mixed with the required amount of aqueous medium and stirred for some time. The aqueous medium is for example a physiological salt solution (0.9 wt. % NaCl) to which the required amount of non-ionic surface acive agent has already been added. Vials can be filled with the suspension thus obtained and sealed.

When the sealed vials have to be sterilized by heating (20 minutes at 121° C.), the problem indicated hereinbefore arises that the suspended particles of the anesthetic melt and wholly or partly flow together. Despite vigorous shaking on cooling it is not possible to get back a suspension of sufficient stability. It was found that when the suspension thus obtained is cooled down further to a temperature below the freezing point of the aqueous medium, for example is frozen in a deep-freezer at a temperature in the range of 0° C. to −25° C., for example −18° C., and subsequently the frozen mixture is defrosted while vigorously shaking the vial mechanically in a shaking machine, the original stable suspension can be recovered. If required the freeze-defrost cycle is repeated one or two times. With this method a great number of vials can be treated simultaneously.

It is also possible to produce the suspensions under sterile conditions so that it is not necessary to sterilize the vials at high temperature. A suspension according to the invention can also be sterilized without melting of the anesthetic, for example sterilization with the aid of gammarays.

Any suitable shaking machine can be used for the above-indicated shaking operation during defrosting of the frozen suspension, for example the "Marius" shaking machine, type 82 SE5. The number of shaking movements per minute may vary and is for example in the range of 300 to 500 movements per minute.

When the sealed vials containing a suspension of a narcotic analgesic have to be sterilized by heating (20 minutes, 120° C.) the aforementioned problems caused by melting of the active substance are not encountered.

The stable aqueous suspensions of water-insoluble local anesthetics obtained according to the invention appear to be very suited for epidural or intrathecal combatting of pain. Tests in dogs showed that epidural administration of a preparation according to the invention led to long-lasting blackade of the sensory nerves without blocking the motor function. Further, it was shown that the used non-ionic surface-active agent did not induce any pathomorphological changes. The preparation was also used in cancer patients suffering from intractable pain caused by intrusion of the tumor in nerve tissue. Drugs such as opiates administered orally and epidurally did not give sufficient relief of pain. On epidural administration of BAB-suspension according to the invention the patients became wholly or essentially pain free for a long time and no detrimental effects of the use were seen.

The invention will be illustrated with the following examples.

EXAMPLE 1

Under aseptic conditions 3 g of sterile BAB having a geometric mean particle diameter of 11–13 μm (corresponding with an arithmic median particle diameter of 16–17 μm) was filled into each of a series of vials of 30 ml, after which the vials were plugged with a rubber stop and sealed with an infusion cap.

Polysorbate 80 and a physiological salt solution (0.9 wt. % NaCl in water) were mixed in a beaker in such proportions that a solution was obtained containing 0.25 mg/ml polysorbate 80. The solution was filtered through a 0.2 mm filter and sterilized (20 minutes, 120° C.). The solution thus obtained was aseptically filled in 30 ml vials.

By injecting under sterile conditions the contents of a vial containing said solution with a syringe into a vial containing 3 g of BAB and shaking for a while a stable suspension of BAB (10 wt. %) was obtained in the latter vial. The suspension remained stable for weeks and can epidurally be administered through a catheter with the aid of syringe. The pH of the suspension was 6.5.

Replacement of BAB with morphine and with a mixture of BAB and morphine (varying in weight ratio from 10:1 to 1:10) gave similar results. The pH of these morphine containing suspensions was adjusted to pH=9.5.

EXAMPLE 2

A sterile aqueous suspension of BAB (10 wt. %) was prepared in a vial of 50 ml by suspending 3 g of BAB in 30 ml of water containing 0.9 wt. % NaCl and 0.025 wt. % polysorbate 80. The vial with its contents was sterilized for 20 minutes at 121° C., after which the vial containing a liquid mixture was cooled to room temperature while vigorously shaken in a mechanical shaking machine (Marius Instruments). Subsequently the mixture was frozen (−18° C.) and then defrosted while again vigorously shaken in said shaking machine. The freese-defrost cycle was repeated twice with vigorous shaking during the defrost period. The result was a 30 ml stable aqueous suspension of BAB having a mean particle diameter of about 15 μm which after gently shaking for a while, even after storage at 4° C. for four weeks, could be administered without any problems through an epidural catheter with the aid of a syringe. The pH of the suspension was 6.5.

Replacement of BAB with EAB and lidocaine, respectively, gave similar results. Replacement of 0.025 wt. % polysorbate 80 with 0.04 wt. % polysorbate 60 gave similar results.

EXAMPLE 3

A sterile aqueous suspension of morphine (10 wt. %) was prepared in a vial of 30 ml by suspending 3 g of morphine having an arithmic median particle size of 16–17 μm in 30 ml of water containing 0.9 wt. % NaCl and 0.025 wt. % polysorbate 80. The pH of the suspension was adjusted to pH 9.5. The vial with its contents was sterilized for 20 minutes at 121° C. Replacement of 0,025 wt. % polysorbate 80 with either 0.05 wt. % polysorbate 80 or 0.05 wt. % polysorbate 60 gave similar results.

EXAMPLE 4

Nine patients suffering from intractable pain due to cancer were treated with the BAB preparation produced in example II. Treatment with epidural BAB via a catheter was ended when adequate pain relief had been obtaind, or when no further improvement or increase in sensory blockade after repeated injections occurred.

Prior to the epidural administration of the BAB suspension eight of the nine patients had an epidural catheter through which 3 mg of morphine in 10 ml of a physiological salt solution (0,9 wt. % NaCl in water) was administered very frequently (6 to 10 times a day). However, pain relief was insufficient. The first patient did not want morphine because of side-effects. She received palliative radiation treatment with the aim to reduce the tumor mass which pressed on the plexus lumbosacralis, in order to give relief of pain. Despite the radiation treatment the tumor mass increaded and so did the pain.

In the table at page 10, data and results of the treatment of these nine patients with the BAB suspension according to the invention are summarized.

In all patients epidural administration of morphine could be stopped. None of the patients showed paralysis after the epidural administration.

In the patients marked *, necropsy was performed. In all these patients, small aggregates of BAB were found in the dorsal subcompartment of the epidural space. The dura, spinal nerve roots, spinal ganglions and the spinal cord did not reveal any abnormality on macroscopic examination. On microscopic examination, no lesions were found in the spinal nerve roots and spinal cord.

The results show that it is possible to obtain long-lasting pain relief up to several months in cancer pain patients after repeated epidural administration of 10% BAB-suspensions according to the invention, without adverse effects. A marked reduction in pain and hence of opioid use could be obtained. Long-lasting sensory blockade to pinprick pain sensibility and cold discrimination without any evidence of motor blockade was established up to several months. Any neurotoxic effects of BAB were not found.

TABLE

| patient | diagnosis | total volume BAB suspension (ml) | n doses during m days (n/m) | result |
|---|---|---|---|---|
| V1 | cervix-ca | 20 | 3/3 | complete relief, no medication, 138 days analgesia T4-L3 |
| V2 | cervix-ca | 15 | 3/3 | died after 5 days no pain |
| V3 | mamma-ca | 21 | 5/2 | complete relief, no medication, 50 days analgesia T8-S4, until death |
| M1* | bladder-ca | 62 | 5/7 | good relief, sporadic 10 mg MS-Contin orally, 20 days analgesia T6-L5, until death |
| M2 | rectum-ca | 26 | 4/4 | fair relief + 40 days analgesia T10-T12 until death |
| M3* | rectum-ca | 48 | 6/6 | complete relief, no medication 71 days analgesia T4-L5, until death |
| M4 | lung-ca | 26 | 4/4 | complete relief, no medication 65 days analgesia T2-L2, until death |
| M5 | bladder-ca | 60 | 4/3 | good relief 2 × 10 mg MS-Contin orally, 36 days analgesia T10-S2, until death |
| M6* | lung-ca | 57 | 5/2 | good relief 2 × 10 mg MS-Contin orally, 36 days analgesia T8-S1, until death |

We claim:

1. An aqueous suspension preparation for injection to combat pain comprising a water-insoluble local anesthetic and/or narcotic analgesic in the form of particles wherein more than 99% of said particles have a diameter of less than 100 μm and more than 90% have a diameter of less than 50 μm, the mean particle diameter being less than 20 μm, said particles being suspended in an aqueous medium wherein the sole agent for stabilizing the suspension is a non-ionic surface-active agent in an amount of less than 1 wt. %.

2. The preparation according to claim 1, wherein said local anesthetic and/or narcotic analgesic is or are present in an amount of from 1 to 15 wt. %.

3. The preparation according to claim 1, wherein said local anesthetic is of the ester-type or of the amide type, or a water-insoluble salt thereof.

4. The preparation according to claim 3, wherein said local anesthetics is a lower alkyl ester of p-aminobenzoic acid.

5. The preparation according to claim 4, wherein said local anesthetic is the n-butylester of p-aminobenzoic acid.

6. The preparation according to claim 1, wherein said narcotic analgesic is a natural or (semi-) synthetic opioid or a water-insoluble salt thereof.

7. The preparation according to claim 1, wherein said non-ionic surface-active agent comprises a polyoxyalkylene ether of a polyhydroxy alcohol which is partially esterified with a higher fatty acid.

8. The preparation according to claim 7, wherein said non-ionic surface-active agent comprises a polysorbate.

9. The preparation according to claim 8, wherein said non-ionic surface-active agent comprises polysorbate 80.

10. The preparation according to claim 1, wherein said non-ionic surface-active agent is present in an amount of less than 0.4 wt. %.

11. The preparation according to claim 10, wherein said non-ionic surface-active agent is present in an amount in the range of from 0.01 to 0.2 wt. %.

12. The preparation according to claim 1, comprising a mixture of a water-insoluble local anesthetic and narcotic analgesic in a weight ratio from 10:1 to 1:10.

13. The preparation according to claim 1, wherein said aqueous medium is a physiological salt solution or a diluted glucose solution.

14. A process for producing an aqueous suspension preparation for injection to combat pain comprising a water-insoluble local anesthetic and/or narcotic analgesic in the form of particles wherein more than 99% of said particles have a diameter of less than 100 μm and more than 90% have a diameter of less than 50 μm, the mean particle diameter being less than 20 μm, said particles being suspended in an aqueous medium wherein the sole agent for stabilizing the suspension is a non-ionic surface-active agent in an amount of less than 1 wt. %, said process comprising:
   suspending the water-insoluble local anesthetic in powder form in the aqueous medium containing the non-ionic surface-active agent to form a suspension;
   sterilizing the suspension thus obtained at about 120 deg. C. for about 20 minutes to form a wholly liquid mixture;
   cooling the wholly liquid mixture to room temperature while vigorously stirring or shaking said liquid mixture;
   then freezing the cooled liquid mixture at a temperature between 0 deg. C. and −25 deg. C. to form a frozen mixture; and
   defrosting the frozen mixture while vigorously shaking the frozen mixture.

15. The process according to claim 14, wherein the freeze-defrost cycle is repeated once or twice while the mixture is vigorously shaken during the defrost period.

16. A method for epidurally treating pain in patients in need for pain relief, comprising administering epidurally to said patient an aqueous suspension preparation for injection to combat pain comprising a water-insoluble local anesthetic and/or narcotic analgesic: in the form of particles wherein more than 99% of said particles have a diameter of less than 100 μm and more than 90% have a diameter of less than 50 μm, the mean particle diameter being less than 20 μm, said particles being suspended in an aqueous medium wherein the sole agent for stabilizing the suspension is a non-ionic surface-active agent in an amount of less than 1 wt. %.

* * * * *